(12) United States Patent
Lu et al.

(10) Patent No.: US 6,204,383 B1
(45) Date of Patent: Mar. 20, 2001

(54) PROCESSES FOR PREPARING SILDENAFIL

(75) Inventors: Yee-Fung Lu, Scarborough; Casimir Antczak; Jan Oudenes, both of Aurora; Yong Tao, Richmond Hill, all of (CA)

(73) Assignee: Torcan Chemical Ltd., Aurora (CA)

( * ) Notice: Subject to any disclaimer, the term of this patent is extended or adjusted under 35 U.S.C. 154(b) by 0 days.

(21) Appl. No.: 09/089,411

(22) Filed: Jun. 3, 1998

(30) Foreign Application Priority Data

May 15, 1998 (AR) .............................. 980102272

(51) Int. Cl.[7] ....................... C07D 487/04; C07D 231/40
(52) U.S. Cl. ......................... 544/262; 548/371.7
(58) Field of Search ............................. 544/262

(56) References Cited

U.S. PATENT DOCUMENTS 5,719,283 * 2/1998 Bell et al. ........................... 544/262
5,955,611 * 9/1999 Dunn et al. ........................ 544/262

FOREIGN PATENT DOCUMENTS 0463756   2/1992   (EP) .
0812845  12/1997   (EP) .

* cited by examiner

*Primary Examiner*—Emily Bernhardt
(74) *Attorney, Agent, or Firm*—Nixon Peabody LLP

(57) ABSTRACT

Sildenafil, a known pharmaceutical chemical useful in treatment of male sexual dysfunction, is prepared by processes in which the final chemical intermediate is of significantly lower basicity than sildenafil itself, so that sildenafil can be extracted in substantially pure form from the organic reaction mixture in which it is made by adding an aqueous medium of appropriately chosen acidic pH and causing phase shift of the sildenafil to occur selectively into the aqueous phase.

10 Claims, 2 Drawing Sheets

PROCESSES FOR PREPARING SILDENAFIL

FIELD OF THE INVENTION

This invention relates to the pharmaceutical chemical 5-[2-ethoxy-5-(4-methylpiperazin-1-yl sulphonyl)-phenyl]-1-methyl-3-n-propyl-1,6-dihydro-7H-pyrazolo[4,3-d]pyrimidin-7-one, known generically as sildenafil, and more specifically to novel processes for preparing sildenafil.

BACKGROUND OF THE INVENTION AND PRIOR ART

Sildenafil, of structural chemical formula:

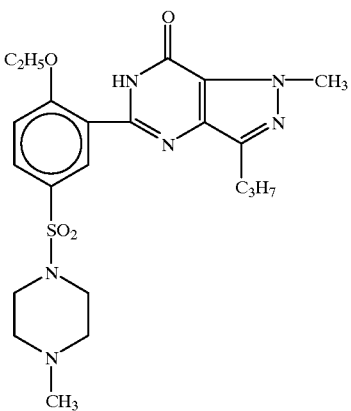

is known, from e.g. European Patents EP-A-0463756 and EP-A-0812845. It has pharmaceutical utility in the treatment of male sexual dysfunction.

As a relatively complicated synthetic organic chemical molecule, sildenafil requires a multi-step chemical synthesis.

Any organic synthesis step, which is part of a complex multi-step synthesis, results in contamination of the intermediate with solvents, catalysts, starting materials and by-products and so introduces the requirement for purification. If a pharmaceutical grade of final product is to result, this cleaning must be done either as the contamination is caused, that is in the work-up of the particular step, or at some subsequent point in the process. A rugged process is desirable which is not demanding with regard to the purity of the intermediates and which allows for a very efficient cleaning during the isolation of the final drug product.

It is an object of the present invention to provide novel processes for preparing sildenafil which simplify the purification procedures and which produce sildenafil in substantially pure form without involving complex purification procedures.

It is a further object of the present invention to provide intermediates useful for the preparation of sildenafil by such novel processes.

SUMMARY OF THE INVENTION

The process of the present invention utilizes, as its last synthetic step, a reaction involving an intermediate of significantly less basicity than sildenafil itself, followed by phase shifting, according to which the sildenafil moves exclusively from the reaction mixture phase to an added, immiscible phase.

The phase shifting can be done in either of two ways, both of which are envisioned to fall within the scope of this invention. In the first way, the more basic tertiary amine functionality which is introduced into sildenafil in the last step is used to extract sildenafil into a predominantly aqueous phase by adjusting the pH of the aqueous phase to less than about 2.7. The less basic by-products and contaminants commingling with sildenafil can be extracted therefrom with common organic solvents essentially immiscible with the predominantly aqueous acid phase. It is essential to the invention that in this extractive purification the more basic functionality is introduced or unmasked in the last synthetic step, the step in which sildenafil is itself created. It is only thus that the benefit of highly pure sildenafil is obtained. An extensive description of methodology for determining preferred conditions for separating a more basic amine from less basic amines is more fully described by Arne Brandstrom in Acta Chem. Scand. B 33(1979) 731–734 which is incorporated herein by reference. In the second way to use phase shifts to purify sildenafil the crude substance along with all the residual starting materials, reagents and by-products are partitioned between a mixture of 1:1 v/v 85% phosphoric acid-water and an immiscible unreactive organic solvent. The phosphoric acid causes the sildenafil to dissolve completely in the predominantly aqueous phase. Non-basic impurities are extracted into the organic layer which is separated. A halogenated organic solvent such as chloroform, methylene chloride or the like is then added to the aqueous phosphoric acid containing phase followed by a molar equivalent compared to sildenafil of a salt of a monoanion, such as sodium bromide, sodium iodide, sodium nitrate, sodium thiocyanate, tetrafluoroborate, perchlorate or the like. The sildenafil ammonium cation with this-monoanion will be selectively extracted into the organic halogenated solvent. Low molecular weight basic compounds will not be so extracted nor will weakly basic compounds nor will salts of primary and secondary amines even if these compounds are strong bases. Thus the sildenafil is separated by simple ion pair extraction from several classes of impurities. The sildenafil itself can easily be recovered by basification and reextraction into an organic solvent from which it can be isolated either by crystallization or evaporation as desired. Further details useful for understanding the many ways the invention can be practiced can be found in an article entitled, "A Convenient Method for the Preparation of Salts of Amines," Acta. Chem. Scand. 23(1969) 1215–18 incorporated herein by reference.

Accordingly, in such process, in one embodiment of the invention, the sildenafil can be extracted from the organic medium in which it is prepared, with an aqueous solvent, with appropriately chosen pH, so that a phase shift takes place whereby the desired end product is caused to move from one phase of the reaction medium to another, whilst unchanged reactants and other by-products are left in the original, organic phase of the reaction medium.

According to a second embodiment of the invention, the sildenafil can be extracted from a predominantly aqueous acid solution containing a large lipophilic monoanion with a halogenated organic solvent so that a phase shift takes place whereby the desired end product as an ammonium salt ion pair is caused to move from one phase of the reaction medium to another, whilst unchanged reactants and other by-products are left in the original aqueous acidic phase of the reaction medium. The ion pair is then neutralized and recovered. As a result, in all embodiments the process leads to the production of sildenafil in a very high degree of purity, whilst minimizing the number and complexity of the purification steps required.

Thus, according to one embodiment of the present invention, there is provided a process for preparing sildenafil in solution in an organic solvent and subsequently recovering the sildenafil from an organic solvent, characterized by converting a chemical intermediate of substantially lower basicity than sildenafil, by appropriate chemical reaction in an organic reaction medium, to sildenafil, treating the resultant sildenafil-containing reaction medium with an aqueous liquid medium containing a strong acid and a large lipophilic monoanion, separating the original reaction solvent, adding a halogenated organic solvent so as to cause a phase shift whereby the sildenafil ammonium anion pair with the monoanion is transferred from the aqueous phase to the halogenated organic phase to the exclusion of other, significantly less basic components of the reaction mixture, neutralizing the salt with organic base, washing out the inorganic salts with water and recovering the sildenafil from the organic halogenated phase.

DESCRIPTION OF THE PREFERRED EMBODIMENTS

Figure 1:
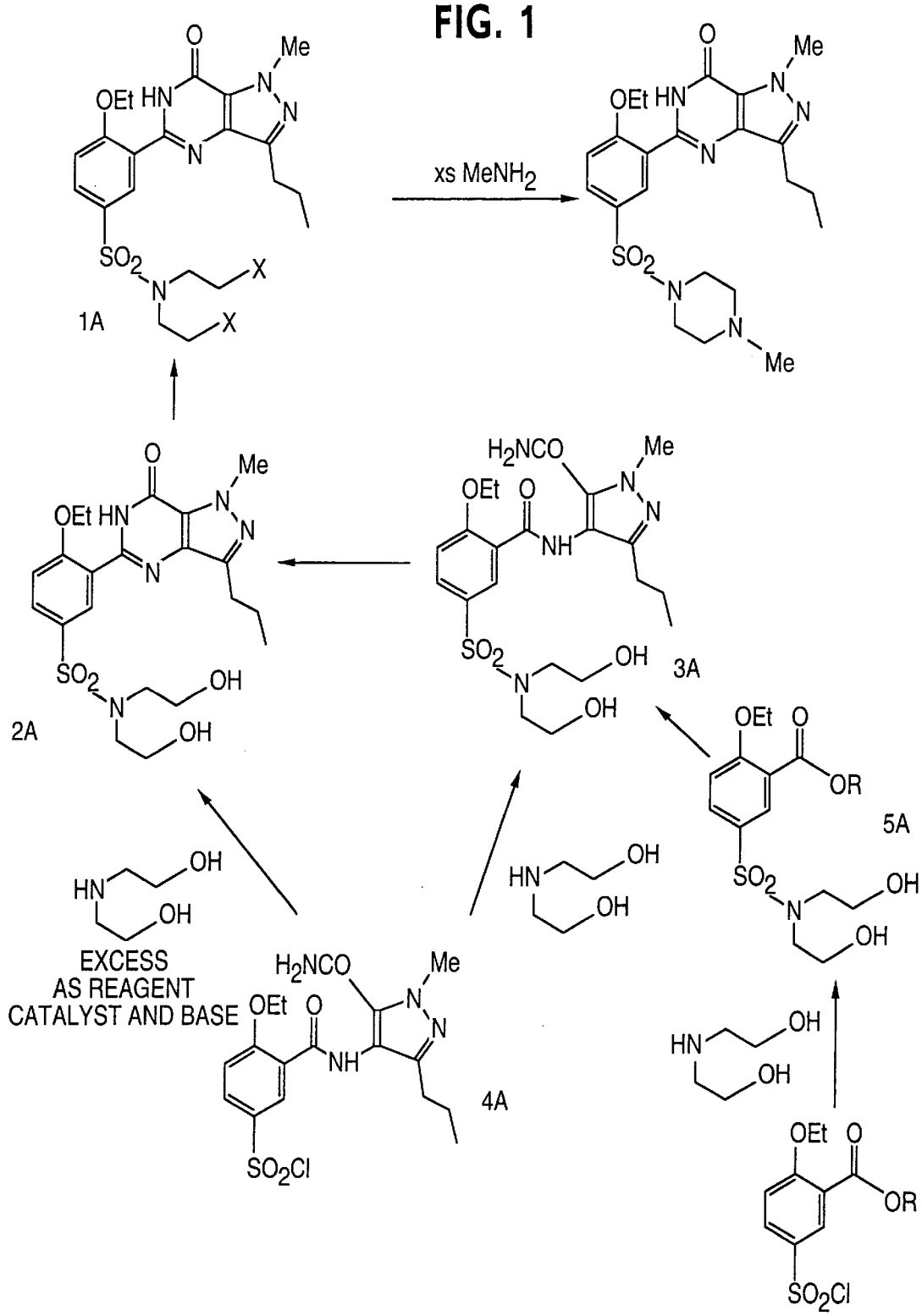
FIG. 1 is an illustration of a chemical reaction synthesis scheme which includes a first preferred process according to the present invention.

In a first preferred process according to the invention, the final step is a ring closure of a tertiary amine compound to form the required, piperazine ring of sildenafil, as illustrated in FIG. 1 of the accompanying drawings, the last chemical synthesis step on that Figure. Chemical group X on final intermediate 1A on FIG. 1 represents a reactive functionalized hydroxyl group, such as methyl sulfonyloxy (mesylate), benzene sulfonyloxy (besylate) or toluene sulfonyloxy (tosylate). The intermediate 1A is prepared in solution in an organic solvent, and methyl amine is added as a solution in an organic solvent. Then the sildenafil product is extracted with an aqueous solvent of appropriately chosen pH. A phase shift takes place whereby the desired end product sildenafil is taken into aqueous solution at a controlled pH. The much less basic intermediates which do not contain a tertiary alkyl amine, i.e. do not contain the N-methyl substituted piperazine group, are left in the organic medium.

Intermediate 1A used as the final intermediate in the process shown on FIG. 1 is, typically, 5-[5-(bis-(2-hydroxyethyl)amino)sulfonyl]-ethoxy)phenyl]-1-methyl-3-n-propyl-1,6-dihydro-7H-pyrazolo[4,3-d]pyrimidin-7-one, i.e. the compound shown as 1A in FIG. 1 where X is methylsulfonyloxy. The closure of the piperazine ring using methylamine to form the 4-N-methyl substituted ring introduces the strongly basic tertiary amino group at that position, so that the resulting sildenafil is much more strongly basic than intermediate 1A. Consequently, sildenafil can be simply separated therefrom by extraction with aqueous liquid of pH from 1.7 to 2.7 to cause clean phase shift of the sildenafil to the aqueous phase.

Intermediate 1A in the process shown in FIG. 1 is prepared by standard methods of organic synthesis (conversion of hydroxy to methylsulfonyloxy, by use of mesyl chloride and a hindered tertiary base, for example), from 5-[5-(bis-hydroxy(methylsulfonyloxy)ethyl)amino)sulfonyl]2-ethoxy)phenyl]-1-methyl-3-n-propyl-1,6-dihydro-7H[4,3-d]-pyrimidine-7-one, intermediate 2A shown on FIG. 1. This intermediate is also lacking the strongly basic tertiary amine group of sildenafil. Accordingly, any residues of intermediate 2A will be separated from sildenafil in the final phase shift process, along with residues of intermediate 1A.

Alternative processes are shown on FIG. 1 for preparing intermediate 2A. The first, and simplest, involves reaction of 4-((2-ethoxy-5-chlorosulfonyl)phenyl)carboxyamino-1-methyl-3-n-propyl-5-amido-pyrazole, intermediate 4A on FIG. 1, with excess diethanolamine. In the reaction, diethanolamine acts as both catalyst and reagent, to replace the halide of the halosulfonyl group with the required N-diethanolamine of intermediate 2A, and to close the carboxyamino, 5-amido substituent groupings to form the required pyrimidine ring structure. One alternative shows the use of substantially stoichiometric amounts of diethanolamine reacting with intermediate 4A so as to effect the diethanolamine substitution on the benzene sulfonyl group but not the catalyzed ring closure, and thereby produce intermediate 3A on FIG. 1, namely: 4-(2-ethoxy-5-((N-diethanolamine)sulfonyl)phenyl)carboxyamino-5-amido-3-n-propyl-1-methyl-pyrazole. Intermediate 3A is also preparable by reaction of 1-(lower alkyl ester)-2-ethoxy-5-chlorosulfonyl benzene with diethanolamine to form 1-(lower alkyl ester)-2-ethoxy-5-(N-diethanolamine)sulfonyl benzene, Intermediate 5A, and thence to intermediate 3A by reaction with 1-methyl-3-n-propyl-4-amino-5-amido-pyrazole. The reactions in the above schemes as depicted on FIG. 1 are all standard procedures of organic chemistry, readily workable by one skilled in the art, and to be found in standard reference works on organic chemistry such as Fieser & Fieser "Reagents for Organic Synthesis". None of the chemical reagents or intermediates shown in FIG. 1 have the very basic tertiary amine group of sildenafil. Accordingly sildenafil is much more basic than any of the intermediates in its synthesis, and is readily extracted and purified by phase shift processes described above.

In a second preferred process according to the invention, the final step comprises reduction of an aldehyde or ester group at position 4 of the piperazine ring to the required methyl group of sildenafil, using a reactive hydride donor reagent. This is illustrated as the final step of the reaction scheme set forth in FIG. 2 of the accompanying drawings. Chemical group Y on final intermediate 1B represents CHO or COOR, where R can be, for example, lower alkyl such as ethyl or methyl. The final intermediate 1B is reacted in organic solvent with the hydride donor reagent, for example lithium aluminum hydride or sodium borohydride in acetic acid. Thus, a neutral N-formyl or N-carboalkoxy protected group is converted, in this last reaction step, to sildenafil which, with its tertiary amine group, is much more basic that predecessor intermediate 1B Accordingly, on adding an aqueous extraction solvent of appropriate pH, sildenafil dissolves selectively in the aqueous phase, while unreacted intermediate 1B and any other components of the reaction mixture lacking the tertiary amine group remain dissolved in the organic phase.

Figure 2:
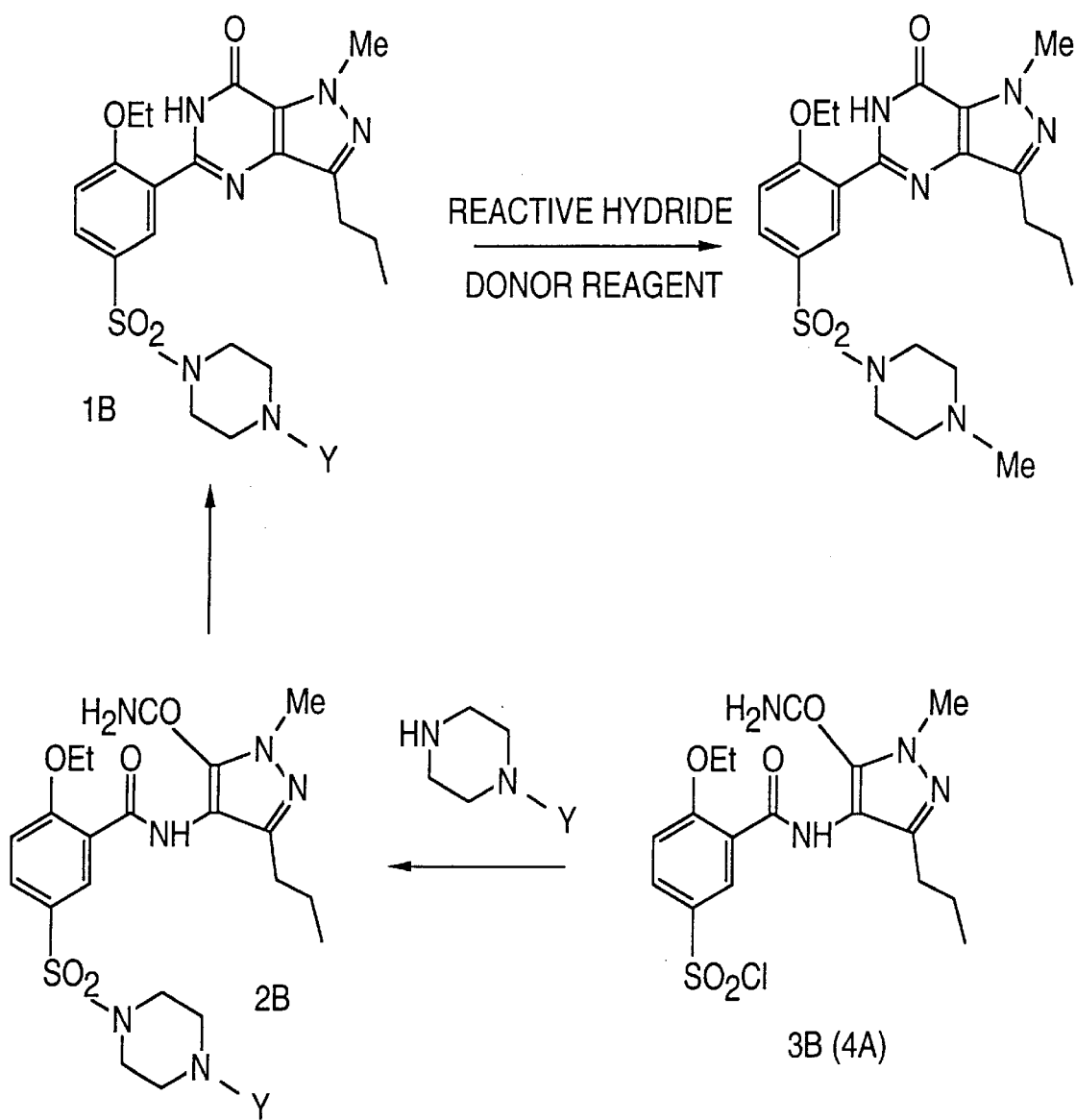
FIG. 2 is a similar illustration of a chemical reaction synthesis scheme which includes a second preferred process according to the present invention.

In this second process according to the invention, intermediate 1B can be prepared in two steps from the same starting material, 4A, labeled 3A in FIG. 2, namely 4-((2-ethoxy-5-chlorosulfonyl)phenyl)carboxyamino-1-methyl-3-n-propyl-5-amido-pyrazole. The first step involves reaction with N-formyl or N-lower alkyl ester-piperazine to form intermediate 2B, namely 4-((2-ethoxy-5-(4-formyl or ester) piperazin-1-yl-sulfonyl)phenyl)carboxyamino-1-methyl-3-n-propyl-5-amidopyrazole. Intermediate 2B is then reacted by methods known per se, e.g. treatment with sodium alkoxide, to form intermediate 1B, namely 5-(2-(ethoxy-5-(4-(formyl or ester)piperazin-1-yl-sulphonyl)phenyl)-1- methyl-3-n-propyl-1,6-dihydro-7H-pyrazolo[4,3-d]
pyrimidine-7-one.

As in the case of a synthetic route shown on FIG. 1, none of the intermediates shown on FIG. 2 has a tertiary amine group equivalent in basicity to the N-methyl substituted pyrazine group of sildenafil. Accordingly, sildenafil after its formation in the last step of the synthesis can be extracted selectively by phase shift using an aqueous medium of appropriately chosen pH, e.g. 1.7–2.7 to free it from residues of any of the precursor intermediates. Again, the chemical reaction steps are standard, routine chemistry, to be found in standard reaction textbooks.

Starting material intermediate 4A (3B) shown on the accompanying drawings, is a novel compound forming an aspect of the present invention. It can also be prepared using standard reactions of organic chemistry, for example from 2-ethoxy-5-chlorosulphonyl-benzoic acid (or acid chloride), a known compound, by reaction with appropriately protected 1-methyl-3-n-propyl-4-amino-5-amido-pyrazole, prepared from pyrazole by methods known per se.

SPECIFIC DESCRIPTION OF THE BEST MODES

The process of the invention is further described in the following non-limiting examples:

EXAMPLE 1

3.3 g, 6.0 mmoles of methylethyl-4-((4-ethoxy-3-(1-methyl-3-n-propyl-1,6-dihydro-7H-pyrazolo[4,3d]pyrimidin-7-onyl)phenyl)sulfonyl)piperazinecarboxylate C24H32N6O6S is dissolved in 250 ml of dry tetrahydrofuran and with stirring at 20–25° C. and 0.56 g, 15 mmoles of lithium aluminum hydride is added and the mixture stirred at this temperature. When TLC of a quenched aliquot shows that the product is formed and the starting material is essentially consumed, the mixture is cooled to 0° C. and quenched by careful addition of 1.7 g of sodium sulfate decahydrate. The slurry is stirred until the solid turns white. The slurry is filtered and the solid placed in a Soxhlet extractor and continuously extracted with 200 ml of diethyl ether. The THF and the ether extract are combined and concentrated. The crude product is mixed with 100 ml of methylene chloride and 100 ml of water with stirring and the pH of the aqueous phase is adjusted to 1.7–2.7 by dropwise addition of methanesulfonic acid. When the aqueous phase pH is stable in this range, the methylene chloride phase is separated. 50 ml of fresh methylene chloride is added and the two phases shaken vigorously in a separatory funnel. If the pH moves outside the set range the pH is adjusted. The methylene chloride is again separated. 90 ml of fresh methylene chloride and 10 ml of methanol is added to the aqueous phase in a stirred flask and aqueous sodium hydroxide is added to the stirred phases until the pH is 8.0–8.5. The methylene chloride-methanol layer which contains the product is separated and the solvent mixture evaporated to yield solid purified sildenafil.

EXAMPLE 2

6.36 g of 5-[5-((bis(2-(methylsulfonyloxy)ethyl)amino)sulfonyl)-2-ethoxyphenyl]-1-methyl-3-n-propyl-1,6-dihydro-7H-pyrazolo[4,3d]pyrimidine-7-one is dissolved in 50 ml of ethanol. To this solution at 40–45° C. is added gradually by syringe pump 5 ml of 8.03 M methylamine in ethanol which is further diluted to a total volume of 25 ml. The addition took place over 12 hours. The reaction is followed by appearance of product according to TLC [70/30/1 v/v/v toluene/methanol/triethylamine]. At the completion of the reaction the solvent is stripped and the crude mixture dissolved in 100 ml of 1:1 v/v 85% phosphoric acid and water. 100 ml of methylene chloride is added and with stirring 1.5 g (0.01 moles) of sodium iodide is added. The solid dissolves and the two liquid phases are stirred vigorously together. The aqueous phase is separated and the methylene chloride dried with anhydrous magnesium sulfate. The hydroiodide of sildenafil is in the methylene chloride. 10 ml of methanol is added and the hydroiodide neutralized by the addition of 50% aqueous sodium hydroxide. The solution is filtered to remove sodium iodide and traces of water. Evaporation yields purified sildenafil.

EXAMPLE 3

To 4.79 g, 0.01 moles of 5-[5-((bis(2-hydroxyethyl)amino)sulfonyl)-2-ethoxyphenyl]-1-methyl-3-n-propyl-1,6-dihydro-7H-pyrazolo[4,3d]pyrinidin-7-one dissolved in 100 ml of dry methylene chloride is added 2.12 g (0.021 moles) of triethylamine which had been dried over solid sodium hydroxide. To the mixture is added 0.04 g of 4-dimethylaminopyridine. The entire reaction mixture is stirred under nitrogen and cooled to −20° C. Methanesulfonylchloride (2.45 g, 1.66 ml, 0.021 moles) dissolved in 25 ml of dry methylene chloride is added dropwise maintaining the temperature at −20° C. After stirring for 2–6 hours the formation of product is checked by TLC and if complete the reaction is adjusted to 0–+5° C. and washed with 2×25 ml of water. The solution is dried with sodium sulfate and evaporated without heat to give the product.

EXAMPLE 4

The reaction mixture obtained in Example 3 after reaction completion is warmed to 20–25° C. and it is gradually with stirring over 12 hours treated with 4.0 ml (0.032 moles) of 33% methylamine in ethanol which is diluted to a total volume of 25 ml with ethanol. When the product had formed predominantly as evidenced by TLC [toluene/methanol/ethylamine 70/30/1 v/v/v on silica gel], 100 ml of water is added to the reaction flask and the pH of the aqueous phase adjusted using 50% aqueous sodium hydroxide to 8.0–8.5. The aqueous phase is cut and discarded. 100 ml of water is added to the methylene chloride layer containing the product and the pH of the aqueous layer adjusted to pH 1.7–2.7 by the cautious addition of methanesulfonic acid with continuous stirring. The methylene chloride phase is separated. A second methylene chloride extraction is conducted at pH 1.7–2.7, then 90 ml of methylene chloride and 10 ml of methanol is added to the aqueous layer and the pH adjusted to 8.0–8.5 by addition of 50% aqueous sodium hydroxide. The layers are shaken together in a separatory funnel and the organic layer containing the purified sildenafil removed. The product is isolated by evaporation to dryness.

EXAMPLE 5

5.6 g of ethyl-4-((4-ethoxy-3-(1-methyl-3-n-propyl-1,6-dihydro-7H-pyrazolo[4,3d]pyrimidin-7-onyl)phenyl)sulfonyl)piperazinecarboxylate was placed in a 500 ml round bottomed flask with 60 ml of THF. The suspension was stirred with a magnetic stirrer under nitrogen. 1.14 g of lithium aluminum hydride was added all at once. Bubbling was immediately generated, the THF began to reflux and the suspension became a semi-solution. The colour changed from light brown to pink. TLC eluting with 5:1 v/v methylene chloride/methanol showed that the reaction was complete. The reaction mixture was diluted with 100 ml of methylene chloride and 10 grams of Celite was added. Cautiously 10 g of sodium sulfate decahydrate was added to destroy the excess hydride. After 15 minutes the suspension was filtered through a pad of Celite and washed with methylene chloride. The filtrate was concentrated on the rotary evaporator to an oil. The oil was dissolved in 100 ml of fresh methylene chloride and 60 ml of 10% aq. sodium hydroxide and 10 g of sodium chloride were added and vigorously stirred for 30 minutes. The layers were separated and the organic layer was washed with a little brine. The aqueous phase from the initial cut was back extracted with two 100 ml portions of methylene chloride and all the methylene chloride fractions were combined and dried over magnesium sulfate. The organic layer was filtered and evaporated to give crystalline crude sildenafil about 3.4 g.

EXAMPLE 6

12.9g of 5-[5-((bis(2-(methylsulfonyloxy)ethyl)amino)sulfonyl)-2-ethoxyphenyl]-1-methyl-3-n-propyl-1,6-dihydro-7H-pyrazolo[4,3d]pyrimidin-7-one is dissolved in 300 ml of ethanol in a 51L r.b. flask equipped with a magnetic stirrer, nitrogen purge and reflux condenser. To this solution at 20–25 C is added 10 ml of diisopropylethylamine and 120 ml of 8.03M methylamine in ethanol. The reaction mixture was warmed to 40 C. The appearance of product according to TLC [70/30/1 v/v/v toluene/methanol/triethylamine]. Evaporation of the reaction mixture to an oil under vacuum and high vacuum. The crude mixture dissolved in 100 ml of 1:1 v/v 85% phosphoric acid and water. 100 ml of methylene chloride is added and with stirring 1.5 g(0.01 moles) of sodium iodide is added. The solid dissolves and the two liquid phases are stirred vigorously together. The aqueous phase is separated and the methylene chloride dried with anhydrous magnesium sulfate. The hydroiodide of sildenafil is in the methylene chloride. 10 ml of methanol is added and the hydroiiodide neutralized by the addition of 50% aq. Sodium hydroxide. The solution is filtered to remove sodium iodide and traces of water. Evaporation yields purified sildenafil.

EXAMPLE 7

To 9.4 g, 19.6 mmoles of 5-[5-((bis(2-hydroxyethyl)amino)sulfonyl)-2-ethoxyphenyl]-1-methyl-3-n-propyl-1,6-dihydro-7H-pyrazolo[4,3d]pyrimidin-7-one slurried in 200 ml of dry methylene chloride was added 5.56 g(43 mmoles) of diisopropylethylamine. The entire reaction mixture is stirred under nitrogen and cooled to 0 C. Methanesulfonylchloride (4.74 g, 3.2 ml, 41 mmoles) was added maintaining the temperature at 0 C. After stirring for 15 minutes at 0 C the mixture was warmed to 20–25 C and left stirring for 16 hours. The formation of product is checked by TLC. The reaction is quenched with 200 ml of water and the biphasic mixture stirred for 10 minutes and cut. The aqueous layer was extracted twice with 200 ml of 9:1 methylene chloride/methanol and all the organic extracts were combined. The solution was concentrated on the rotary evaporator to give 12.9 g of solid product.

We claim:

1. A process for preparing sildenafil, 5-[2-ethoxy-5-(4-methyl piperazin-1-yl-sulphonyl)-phenyl]-1-methyl-3-n-propyl-1,6-dihydro-7H-pyrazolo[4,3-d]pyrimidin-7-one, in solution in an organic solvent and subsequently recovering, from organic solution, the sildenafil product, which comprises the steps of reacting a 5-[2-ethoxy-5(di-functionalized hydroxy ethyl)amino sulphonyl)phenyl]-1-methyl-3-n-propyl-1,6-dihydro-7H-pyrazolo[4,3-d]pyrimidin-7-one of structural formula 1A:

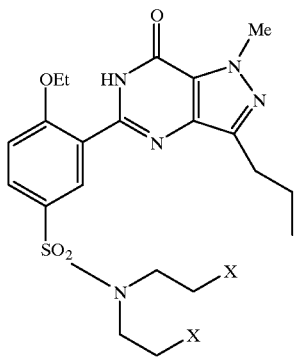

where X represents a reactive functionalized hydroxy, with methyl amine in organic solvent to form sildenafil, treating the resultant sildenafil-containing reaction medium with an aqueous liquid medium of pH from about 1.7–2.7 so as to cause phase shift whereby the sildenafil shifts from the organic phase to the aqueous phase of the resultant mixture to the exclusion of the other, significantly less basic components of the reaction mixture, separating the aqueous phase of the reaction mixture from the organic phase thereof, and recovering substantially pure sildenafil from the aqueous phase.

2. A process for preparing sildenafil, 5-[2-ethoxy-5-(4-methyl piperazin-1-yl sulphonyl)-phenyl]-1-methyl-3-n-propyl-1,6-dihydro-7H-pyrazolo[4,3-d]pyrimidin-7-one, in solution in an organic solvent and subsequently recovering, from organic solution, the sildenafil product, which comprises the steps of reacting a 5-[2-ethoxy-5-(4-formyl or esterified)piperazin-1-yl sulphonyl)phenyl]-1-methyl-3-n-propyl-1,6-dihydro-7H-pyrazolo[4,3-d]pyrimidin-7-one, of formula 1B:

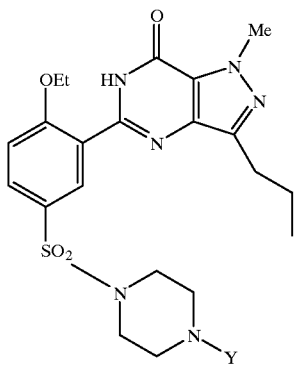

where Y represents CHO or COOR in which R is lower alkyl, with a reactive hydride donor reagent to form sildenafil, treating the resultant sildenafil-containing reaction medium with an aqueous liquid medium of pH from about 1.7–2.7 so as to cause phase shift whereby the sildenafil shifts from the organic phase to the aqueous phase of the resultant mixture to the exclusion of other, significantly less basic components of the reaction mixture, separating the aqueous phase of the reaction mixture from the organic phase thereof, and recovering substantially pure sildenafil from the aqueous phase.

3. The process of claim 1 wherein chemical group X in intermediate 1A is selected from mesylate, besylate and tosylate.

4. The process of claim 2 wherein chemical group R in intermediate 1B is selected from ethyl and isopropyl.

5. The process of claim 4 wherein the reactive hydride donor reagent is lithium aluminum hydride or sodium borohydride.

6. The compound 5-[5-(((bis(2-methylsulfonyloxy)ethyl)amino)sulfonyl)-2-ethoxy-phenyl]-1-methyl-3-n-propyl-1,6-dihydro-7H-pyrazolo[4,3-d]pyrimidin-7-one.

7. The compound 5-[5-((bis(2-hydroxyethyl)amino)sulfonyl)-2-ethyoxy-phenyl]-1-methyl-3-n-propyl-1,6-dihydro-7H-pyrazolo[4,3-d]pyrimidin-7-one.

8. The compound ethyl 4-((4-ethoxy-3-[1-methyl-3-n-propyl-1,6-dihydro-7H-pyrazolo[4,3-d]pyrimidin-7-onyl]phenyl)sulfonyl)piperazinecarboxylate.

9. The compound methylethyl 4-((4-ethoxy-3-[1-methyl-3-n-propyl-1,6-dihydro-7H-pyrazolo[4,3-d]pyrimidin-7-onyl]phenyl)sulfonyl)piperazine-1-carboxylate.

10. The compound 4-((4-ethoxy-3-[1-methyl-3-n-propyl-1,6-dihydro-7H-pyrazolo[4,3-d]pyrimidin-7-onyl]phenyl)sulfonyl)piperazine-1-carboxaldehyde.

* * * * *